United States Patent
Kim et al.

(10) Patent No.: US 10,769,779 B2
(45) Date of Patent: Sep. 8, 2020

(54) METHOD FOR INCREASING READING EFFICIENCY IN MEDICAL IMAGE READING PROCESS USING GAZE INFORMATION OF USER AND APPARATUS USING THE SAME

(71) Applicant: Vuno, Inc., Seoul (KR)

(72) Inventors: Sangki Kim, Seoul (KR); Hyun-Jun Kim, Gyeonggi-do (KR); Kyuhwan Jung, Seoul (KR); Yeha Lee, Gyeonggi-do (KR)

(73) Assignee: Vuno, Inc., Seoul (KR)

( * ) Notice: Subject to any disclaimer, the term of this patent is extended or adjusted under 35 U.S.C. 154(b) by 83 days.

(21) Appl. No.: 15/760,803

(22) PCT Filed: Sep. 24, 2015

(86) PCT No.: PCT/KR2015/010089
§ 371 (c)(1),
(2) Date: Mar. 16, 2018

(87) PCT Pub. No.: WO2017/051944
PCT Pub. Date: Mar. 30, 2017

(65) Prior Publication Data
US 2019/0340751 A1 Nov. 7, 2019

(51) Int. Cl.
*G06F 3/01* (2006.01)
*G06T 7/00* (2017.01)
*G16H 30/20* (2018.01)
*A61B 3/113* (2006.01)
*A61B 5/055* (2006.01)
*A61B 6/03* (2006.01)
*G06F 3/048* (2013.01)

(52) U.S. Cl.
CPC ............ *G06T 7/0012* (2013.01); *A61B 3/113* (2013.01); *G06F 3/013* (2013.01); *G16H 30/20* (2018.01); *A61B 5/055* (2013.01); *A61B 6/032* (2013.01); *G06F 3/012* (2013.01); *G06F 3/048* (2013.01)

(58) Field of Classification Search
CPC ....... G06T 7/0012; G16H 30/20; A61B 3/113; A61B 5/055; A61B 6/032; G06F 3/013; G06F 3/012; G06F 3/048
See application file for complete search history.

(56) References Cited

U.S. PATENT DOCUMENTS

| 2016/0171299 A1* | 6/2016 | Lee ................... G06K 9/00604 382/128 |
| 2016/0314589 A1* | 10/2016 | Nagao .................. G06F 19/321 |
| 2018/0177446 A1* | 6/2018 | Okabe .................... A61B 5/743 |

FOREIGN PATENT DOCUMENTS

| KR | 10-2014-0024788 A | 3/2014 |
| KR | 10-2014-0052263 A | 5/2014 |

(Continued)

*Primary Examiner* — Towfiq Elahi
(74) *Attorney, Agent, or Firm* — IP & T Group LLP (57) ABSTRACT

According to one embodiment, a method for increasing the reading efficiency of a medical image is provided. The method of increasing the reading efficiency of a medical image comprises of: receiving the gaze information of a user, acquiring a gaze tracking device, during a medical image reading process; determining a region of interest of the user with respect to the medical image by using the gaze information; determining a type of service corresponding to the region of interest; and providing the determined service.

17 Claims, 7 Drawing Sheets

(56) References Cited

FOREIGN PATENT DOCUMENTS

| KR | 10-2014-0104163 A | 8/2014 |
|----|-------------------|--------|
| KR | 10-1543947 B1 | 8/2015 |
| WO | 2012-145180 A1 | 10/2012 |
| WO | 2015/143067 A1 | 9/2015 |

\* cited by examiner

METHOD FOR INCREASING READING EFFICIENCY IN MEDICAL IMAGE READING PROCESS USING GAZE INFORMATION OF USER AND APPARATUS USING THE SAME

CROSS REFERENCE TO RELATED APPLICATIONS

This application is a U.S. National Phase Application of International Application No. PCT/KR2015/010089 filed on Sep. 24, 2015. The disclosure of International Application No. PCT/KR2015/010089 is incorporated herein by reference.

TECHNICAL FIELD

The present disclosure relates to a method and apparatus for providing a service aiding in medical image reading to increase reading efficiency.

BACKGROUND ART

Medical imaging apparatuses, including computer tomography (CT), magnetic resonance imaging (MRI), etc., are essential in modern medical science, and the role of clinical diagnoses using medical image instruments in medical activities, which deal with patients' lives is expected to increase, due to advancements in medical technology.

To improve clinical diagnosis, a medical image storage and transmission system (PACS; Picture Archiving and Communication System) is introduced which enables, when necessary, a physician to retrieve a medical image of a subject of interest via a computer monitor in each examination room, after the system converts a medical image (e.g. an X-ray image, CT image, MRI image or ultrasound image) to digital data for databasing and storing it in a large storage medium which is connected to a server.

INVENTION

Technical Problem

Since the brightness of a medical image varies according to the characteristics of a tissue and a subject to examine in the conventional reading process of the medical image, a medical doctor, reading the image, would examine the image while the doctor adjusts the brightness range displayed on a screen.

Whereas, three-dimensional morphology is important in the case of a three-dimensional image, the doctor cannot determine the morphology by only one slice, and thus, the doctor repeatedly must review multiple slices adjacent to the one slice for examination. For example, it is hard to distinguish a blood vessel from a nodule only by a sheet of slice for the case of a nodule, occurred in a lung, so it is necessary to move repeatedly to adjacent slices for examination.

To read a disease objectively, it is necessary to measure a lesion quantitatively, however, there is no choice but to read lesions according to the subjective judgement of a doctor.

Therefore, an unmet need is rising for a method for increasing reading efficiency in the medical image reading process.

Technical Solution

The objective of the present disclosure is to track the gaze of a reader in medical image reading and infer an area which is observed with interest of the reader, for increasing reading efficiency of the medical image.

According to an aspect of the present disclosure, there is a method for increasing medical image reading efficiency, comprising: receiving gaze information from the user, acquiring a gaze tracking device, during the medical image reading process; determining a region of interest with respect to a medical image using the gaze information; determining a type of service corresponding to the region of interest; and providing the determined service.

According to the aspect, the determination of the region of interest may include: generating information on a region of interest based on change of gaze and fixation time of gaze from the gaze information.

Here, the determination of the region of interest may include: analyzing change of the gaze information of the user and inferring a suspected disease from the change of the gaze information.

Further, the providing of the determined service may include: generating quantitative information to aid the reading or diagnosis of the suspected disease.

According to an embodiment of the aspect, the determination of the type of service may include: searching brightness levels and ranges which are required for maximizing the readability of the region of interest.

According to another embodiment of the aspect, the determination of the type of service may include: in the event that the region of interest is a tissue or a lesion, generating three-dimensional information for the tissue or the lesion.

Another embodiment of the aspect is the determination of the type of service that may include: in the event that the region of interest is a tissue or a lesion, generating quantitative information on the tissue or the lesion.

According to yet another embodiment, the determination of the type of service may include: in the event that a lesion or a disease is observed in the region of interest, generating information on temporal change of the lesion or the disease.

According to another aspect of the present disclosure, there is a medical image reading apparatus, comprising: a gaze tracking unit tracking the gaze of a user during the medical image reading process; a service determining unit determining a region of interest of a user with respect to a medical image based on the tracked gaze and determining a type of service corresponding to the region of interest; and a service providing unit providing the determined service.

Here, the service determining unit may generate information on a region of interest based on change of gaze and fixation time of gaze of the user.

Further, the service determining unit may analyze the change of gaze of the user and infer a suspected disease from the change of gaze.

Further, the service providing unit may provide quantitative information to aid the reading or diagnosis of the suspected disease.

Further, the service determining unit may search a brightness level and range which are required for maximizing the readability of the region of interest.

Further, the service determining unit may generate three-dimensional information of a tissue or a lesion, the region of interest is the tissue or the lesion.

Further, the service determining unit may generate quantitative information on a tissue or a lesion, in the event the region of interest is the tissue or the lesion.

Further, the service determining unit may generate information on temporal change of a lesion or a disease, in the event the lesion or the disease is observed in the region of interest.

Advantageous Effects

According to the embodiments of the present disclosure, a reader can read faster and more accurately with respect to the region of interest at which the reader gazes during the reading of a medical image.

According to the embodiments of the present disclosure, the progression of a lesion may be easily analyzed by comparison with a past medical image of the subject.

BEST MODE

Hereinafter, embodiments of the present disclosure will be described in detail with reference to the accompanying drawings.

Figure 1:
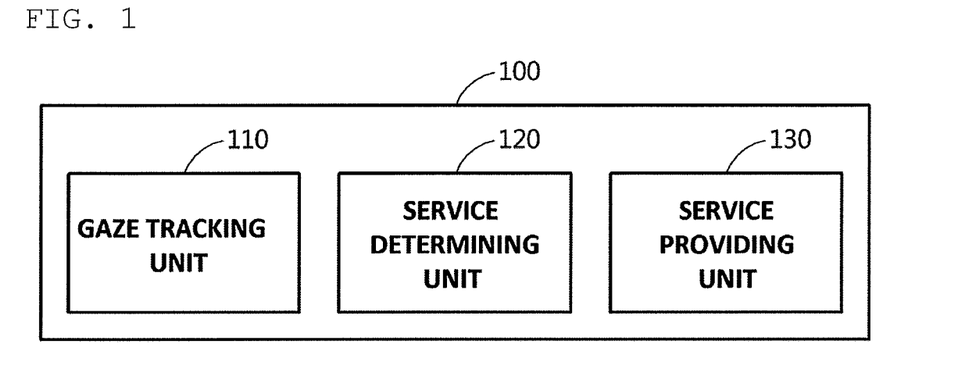
FIG. 1 is a block diagram illustrating a medical image reading apparatus according to an embodiment of the present disclosure.

FIG. 1 is a block diagram for illustrating a medical image reading apparatus according to an embodiment of the present disclosure.

Referring to FIG. 1, the medical image reading apparatus 100 may include a gaze tracking unit 110, service determining unit 120 and service providing unit 130. The medical image reading apparatus 100 may increase reading efficiency of a medical image by using gaze information of a user (e.g. a medical doctor) or a reader to specify a region of interest and providing additional services for aiding the reading of the medical image when the user or the reader reads it.

The gaze tracking unit 110 according to the embodiment may track the gaze of the user, that is, at which portion of the displayed medical image the user gazes. Here, the gaze tracking unit may utilize a conventional eye tracking technology. For example, the gaze tracking unit 110 may track the position at which the user gazes in the medical image displayed in a display (monitor). Further, the gaze tracking unit 110 may track the position at which the user gazes using a camera which takes the pupil movement of the user.

According to another embodiment, the gaze tracking unit 110 may receive gaze information of the user from a separate gaze tracking device. In such a case, the gaze tracking unit functions as a wired or wireless communication unit, which may determine, using the received gazed information, at which portion of the displayed medical image the user gazes.

A service determining unit 120 according to an embodiment may determine the region of interest of the user with respect to the medical image based on gaze information of the user. Here, the gaze information may include gaze information of the user which is tracked by the gaze tracking unit or gaze information of the user which is received by the gaze tracking unit.

According to an embodiment, the service determining unit 120 may generate information on region of interest based on change of gaze and fixation time of gaze of the user. For example, the service determining unit 120 may extract, using the change of gaze of the user, a region of interest (ROI) at which the user gazes with interest for a specific time.

Here, the service determining unit 120 may analyze the change of gaze of the user to infer a suspected disease according to the change of gaze. For example, in the case that the medical image is a lung image of a subject and there is a tumor in the region of interest at which the user gazes, the service determining unit may infer that a cancer is the suspected disease.

The service determining unit 120 according to an embodiment may determine a type of service corresponding to the region of interest of the user. In such a case, the service determining unit 120 may predict the type of service which the user needs currently.

The service determining unit 120 may determine in which department the user or the reader, as a medical doctor, is specialized. Also, the service determining unit 120 may determine for itself what image the displayed medical image is. That is, it may recognize whether the displayed medical image is a two-dimensional image or a three-dimensional image, whether the medical image is an X-ray image, a CT image or an MRI image, and may detect which portion of the body is shown considering the morphology of the medical image.

Further, the service determining unit 120 may determine what the user or the reader is reading and what should be provided thereto. For example, the service determining unit 120 may determine whether a segment of the region of interest should be provided to the user, whether a three-dimensional image should be provided thereto, and whether a similar image of another subject should be provided thereto.

More specifically, the service determining unit 120 may provide a segment of a tumor as a three-dimensional image if the region of interest in the displayed medical image corresponds to the tumor. Further, the service determining unit 120 according to another embodiment may provide, if the region of interest in the displayed medical image indicates a bone fracture, an image in respect of the post-operative prognosis of another subject injured in a similar area.

The service determining unit 120 according to an embodiment may discover whether a brightness level and range, which is required for increasing the readability of the region of interest, is being provided. If the brightness level required for the region of interest is not being provided, the rectified brightness value may be provided through the service providing unit.

The service determining unit 120 according to an embodiment may include a segmentation module extracting the region of interest of the user and enlarging it. Specifically, the segmentation module may extract, with respect to a tissue existing in the region of interest at which the user gazes, the tissue from a current slice as well as from multiple adjacent slices. For example, in the case that the region of interest being currently examined is a blood vessel, the blood vessel may be extracted from upper and lower pieces of slice. For another example, all the regions in slices which includes a spherical nodule may be extracted in the case that the region of interest being currently examined is a nodule.

In such a case, the segmentation module may generate a three-dimensional model by enlarging the region of interest of the user. For example, images, each of which is cropped from each of the segments of adjacent slices with respect to the region of interest may be provided simultaneously. For another example, a model rendered by reconstructing the regions into a three-dimension may be provided. Here, the provision of three-dimensional information may be through a specific area on a screen, and it may be provided by floating it near a tissue being examined in the medical image.

Further, the segmentation module may generate quantitative information of an object of interest (a blood vessel, a nodule, a tumor, etc.) which exists in the region of interest of the user. Also, the segmentation module may extract only the object of interest which exists in the region of interest of the user and trim the rest portion off to provide only the object of interest as an image.

For another example, the service determining unit 120 may generate, in the event that the region of interest is a tissue or a lesion, quantitative information on the tissue or the lesion. Here, the progression of the lesion or a disease may be inferred by comparison with a past history of the region of interest in the case that the past history exists with respect to the tissue or the lesion. Further, the progression of the lesion or the disease may be inferred by comparison with a progression of another subject suffering the same disease.

For another example, a service determining unit 120 may generate, if a lesion or a disease is observed in the region of interest, information on temporal change of the lesion or the disease. More specifically, in the case that a tumor is observed in the region of interest, the service determining unit 120 may discover historical information to generate change in quantitative data, with respect to the past size of the tumor of the same subject, or a three-dimensional model thereof.

The service providing unit 130 according to an embodiment may provide the user with the determined service.

For example, the service providing unit 130 may include a brightness adjusting module adjusting a brightness range and level of the image for increasing the readability of the region of interest. For example, a HU (Hounsfield unit) value adjusted to be adapted for the analysis of a lung image of a subject may be provided, if the user is examining the lung image.

According to an embodiment, the service providing unit 130 may provide quantitative information to aid the diagnosis or the suspected disease which is estimated by the service determining unit 120.

For example, the service providing unit 130 may provide, via a user interface, additional information on a medical image which is a target for examination.

Figure 2:
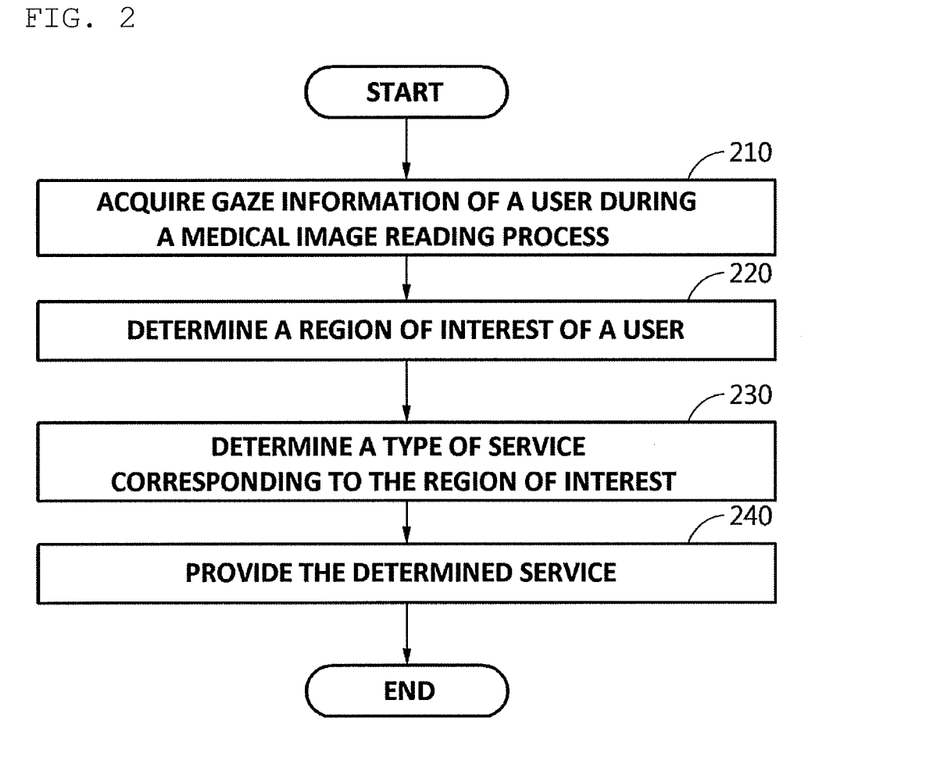
FIG. 2 is a flow chart illustrating a method for increasing medical image reading efficiency according to an embodiment of the present disclosure.

FIG. 2 is a flow chart illustrating a method for increasing medical image reading efficiency according to an embodiment of the present disclosure.

In step 210, the medical image reading apparatus may receive the gaze information of the user which is acquired in the medical image reading process.

According to another embodiment, the medical image reading apparatus may track the pupil movement of the user, reading the medical image, to collect gaze information of the user.

In step 220, the medical image reading apparatus may determine a region of interest of the user with respect to the medical image. For example, information on the region of interest may be generated based on change of gaze movement and fixation time of gaze, which belong to the gaze information of the user.

Here, in step 220, a suspected disease may be inferred according to the change of gaze movement of the user by analyzing the change of gaze movement. If the user fixes the user's gaze at a tumor portion in the medical image, a cancer may be inferred to be a suspected disease.

In step 230, the medical image reading apparatus may determine a type of service corresponding to the region of interest.

Here, the medical image reading apparatus according to an embodiment may search, in the case that the brightness value is not suited for reading an image, a brightness level and range required for maximizing the readability thereof.

The medical image reading apparatus according to another embodiment may generate, in the event that the region of interest is a tissue or a lesion, quantitative information on the tissue or the lesion.

The medical image reading apparatus according to one another embodiment may generate, in the event that a lesion or a disease is observed in the region of interest, information on temporal change of the lesion or the disease.

In step 240, the medical image reading apparatus may provide a reader of the medical image with the determined service.

According to an embodiment, the medical image reading apparatus may set a brightness level and range required for maximizing the readability of the region of interest to provide it.

According to another embodiment, the medical image reading apparatus may provide the user with quantitative information to aid the reading or diagnosis of the suspected disease.

Figure 3:
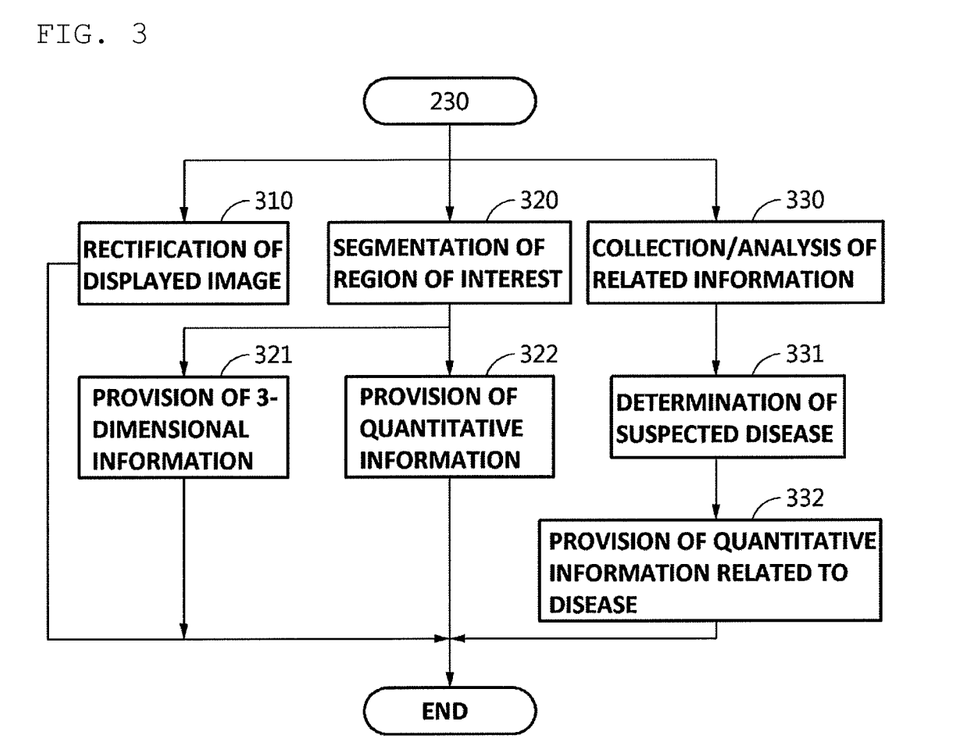
FIG. 3 is a flow chart illustrating how to provide a service which is determined according to an embodiment of the present disclosure.

FIG. 3 is a flow chart illustrating how to provide a service which is determined according to an embodiment of the present disclosure.

In step 310, the medical image reading apparatus according to an embodiment may rectify a medical image which is being displayed. For example, the brightness value, etc., rectified for facilitating the examination of the region of interest at which the user gazes, may be provided.

In step 320, the medical image reading apparatus according to another embodiment may segment the region of interest. Here, the segmentation means cutting the portion corresponding to the region of interest of the image and enlarging it to provide it.

The medical image reading apparatus according to an embodiment may provide additional information for aiding the examination of the segmented region of interest.

In step 321, the medical image reading apparatus may provide three-dimensional information on the region of interest. For example, in the case of searching a lung tumor, a three-dimensional model of the lung tumor may be rendered and provided.

In step 322, the medical image reading apparatus may provide quantitative information on the region of interest. For example, in the case of examining a growth plate of a bone, each bone age and a value of each main part may be displayed and provided.

For example, additional information which is helpful for specifying the type of the region of interest may be provided. For another example, quantitative information may be provided by measuring the size or the volume of the region of interest.

In step 330, the medical image reading apparatus according to another embodiment may collect and analyze information related to the region of interest. During the case, related historical information on the subject may be collected. For example, in the case that a medical image of the patient or the subject had been taken from the same portion of the past, quantitative information, segment information, etc. which relate to the portion corresponding to the region of interest may be collected and analyzed.

In step 331, the medical image reading apparatus may determine a suspected disease which relates to the region of interest. In such a case, the medical image reading apparatus may provide the user with the suspected disease using collected information related to the region of interest and assign a confidence value with respect to the suspect disease.

In step 332, the medical image reading apparatus may provide quantitative information related to the suspected disease.

For example, the medical image reading apparatus may retrieve past history with respect to a course of progression of the suspected disease in the region of interest to provide information on temporal change thereof. That is, it may be provided to the user, by prediction, how further the disease is being progressed since the size of a past tumor of a subject is x and the size of the current tumor of the subject is y, and how will the progression be in the future.

For another example, in the case of measurement of bone density of an osteoporosis patient, the medical image reading apparatus may search an image of another subject having similar conditions to provide it.

Figure 4:
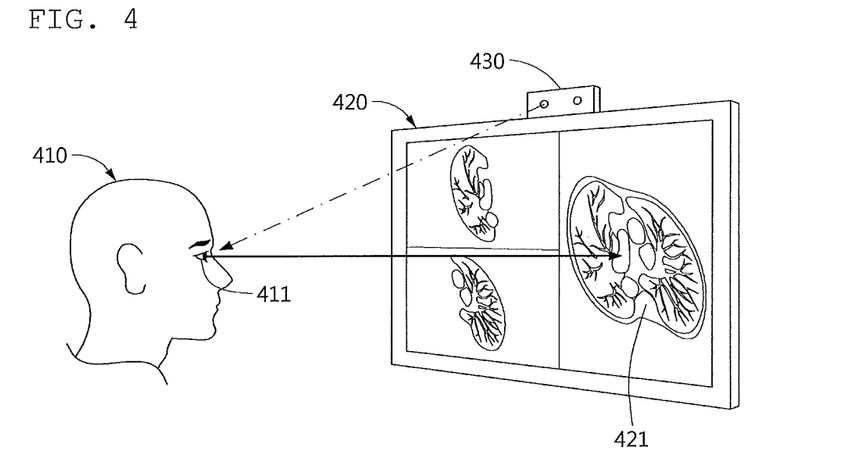
FIG. 4 is a diagram illustrating how a medical image reading apparatus tracks a gaze of a reader according to an embodiment of the present disclosure.

For one another example, if there is a past medical image of the same subject, the medical image reading apparatus may track automatically the portion, which experienced the most change and indicated it FIG. 4 is a diagram illustrating how a medical image reading apparatus tracks a gaze of a reader according to an embodiment of the present disclosure.

Referring to FIG. 4, shown is a situation in which a user 410 reads a medical image through a display apparatus 420 providing the medical image.

The process which analyzes gaze of the user 410 may at first determine what a target image displayed on the display apparatus 420 is. First, whether the target image is a lung image, an eye image or a brain image may be determined.

A gaze tracking unit 430 of the medical image reading apparatus may sense a pupil 411 of the user 410 to track the gaze of the user. For example, in FIG. 4, the gaze tracking unit 430 may sense that the user gazes at the center portion 421 of an object which is displayed on the right in the medical image.

The tracked gaze of the user may be mapped on the medical image. The gaze tracking unit 430 of the medical image reading apparatus may extract the region of interest at which the user gazes by a series of processes.

Figure 5:
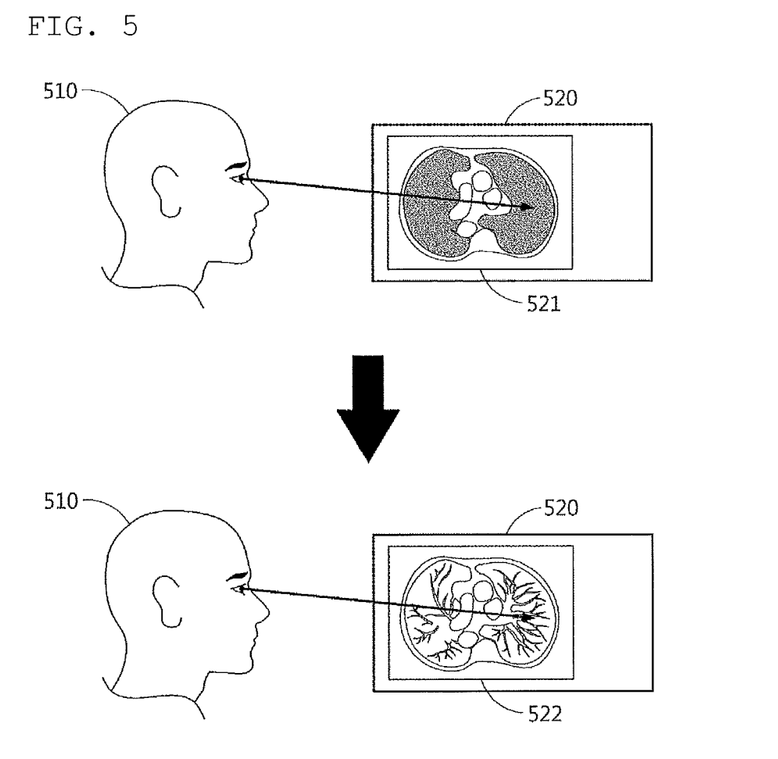
FIG. 5 is a diagram illustrating how to maximize the readability of the region of interest based on tracking a gaze of a user according to an embodiment of the present disclosure.

FIG. 5 is a diagram illustrating how to maximize the readability of the region of interest based on tracking a gaze of a user according town embodiment of the present disclosure.

Referring to FIG. 5, shown may be a situation in which a user 510 gazes at a medical image being provided through a display 520 of the medical image reading apparatus. With the situation, the medical image reading apparatus may identify a portion at which the user gazes in the medical image 512. Regarding to gaze tracking technology, a variety of conventional gaze tracking technologies may be used.

A CT image and X-ray image are shown to be darker as X-rays are transmitted more and whiter as it is transmitted less. Therefore, in the medical image 521, a bone or an organ is shown to be whiter while a portion through which X-ray is well transmitted is shown to be darker.

According to an embodiment, the image displayed in the display 520 may be a lung image of a human. In the past, the brightness value of the image varied according to the characteristics of a tissue to be examined or a subject, and thus, a reader and users examined the image while they adjusted the brightness value of the image displayed on a screen during reading of the medical image. If the portion, at which the user 510 gazes, of a lung image 521 corresponds to the periphery of the lung, the image reading apparatus according to the embodiment may allow the lung image 512, the brightness value of which is rectified, to be displayed by adjusting the brightness level and the brightness representative range of the displayed image to be adapted for the reading of the periphery of the lung.

Figure 6:
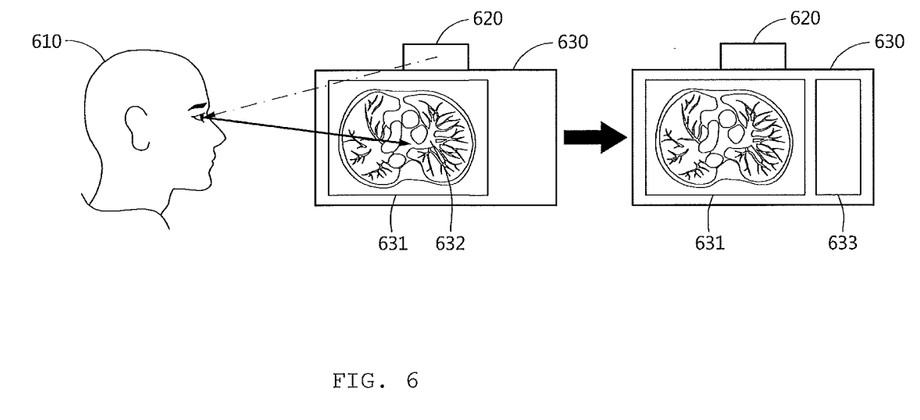
FIGS. 6 and 7 are diagrams illustrating how to provide additional information which relates to a region of interest based on tracking the gaze of the user according to an embodiment of the present disclosure.
Figure 7:
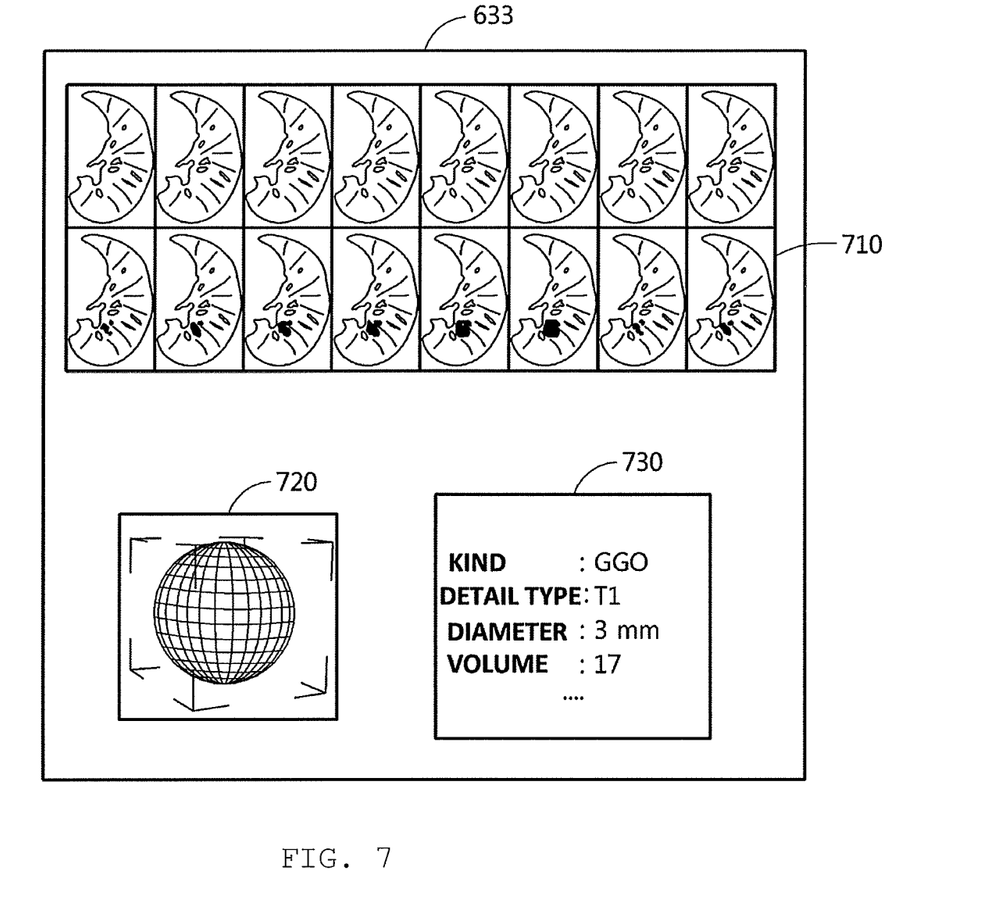

FIGS. 6 and 7 are diagrams illustrating how to provide additional information which relates to a region of interest based on tracking the gaze of the user according to an embodiment of the present disclosure.

Referring to FIG. 6, shown may be a situation in which a user 610 gazes at a medical image 631 being provided through a display 630 of the medical image reading apparatus. The gaze tracking device 620 may track the pupil movement of the user 610 to detect that the user 610 gazes a specific portion 632 of the medical image 631. Here, the gaze tracking device may include gaze tracking devices, according to a variety of conventional methods.

According to an embodiment, the image displayed on the display 630 may be a lung image of a human. If a lesion occurs in the portion 632, at which the user 610 gazes, of the lung image 631, the image reading apparatus may provide additional information 633.

Referring to FIG. 7, additional information 633 according to an embodiment may include segment information 710 in adjacent slice images with respect to a region of interest.

The additional information 633 according to another embodiment may include three-dimensional model 720 which models a segment region with respect to the region of interest.

The additional information 633 according to one another embodiment may include quantitative analysis information 730 of the region of interest. In the past, the condition of a subject was diagnosed by analyzing the size of a tumor depending on the subjective determination of the reader. However, the image reading apparatus according to the embodiment of the present disclosure may be capable to determine a lesion or a disease more accurately because it may quantify the size of the tumor which occurs in the region of interest of the subject to provide it.

Figure 8:
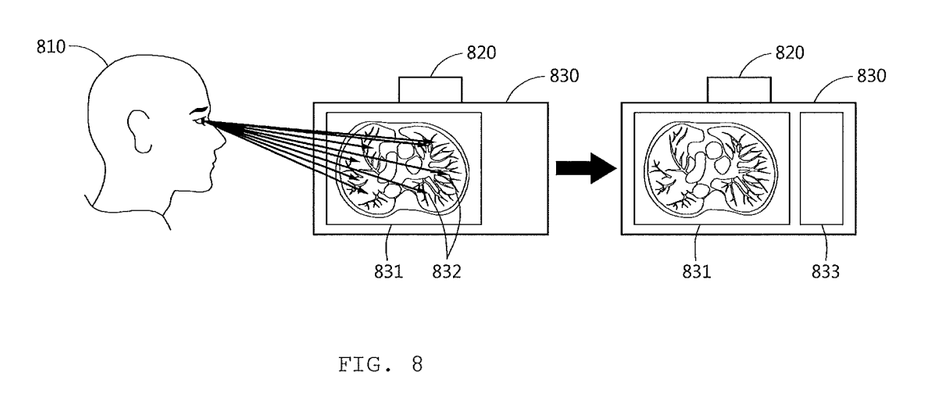
FIGS. 8 and 9 are diagrams illustrating how to provide disease-related information, which relates to a region of interest, based on tracking the gaze of the user according to an embodiment of the present disclosure.
Figure 9:
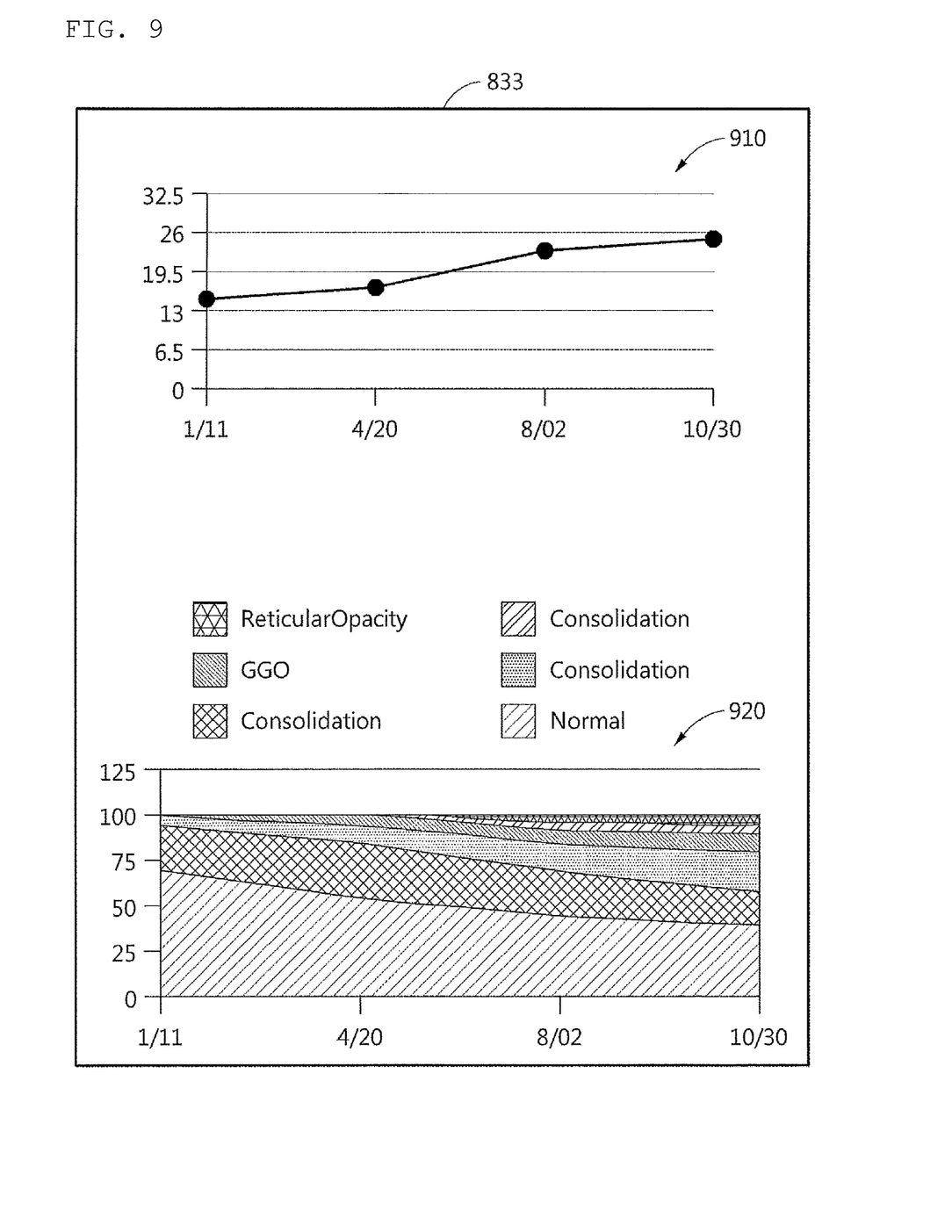

FIGS. 8 and 9 are diagrams illustrating how Oto provide disease-related information which relates to a region of interest based on tracking the gaze of the user according to an embodiment of the present disclosure.

Referring to FIG. 8, shown may be a situation in which a user 810 gazes at a medical image 831 being provided through a display 830 of the medical image reading apparatus. The gaze tracking device 820 may track the pupil movement of the user 810 to detect that the user is examining specific portions 832 of the medical, image 831. Here, the gaze tracking device may include graze tracking devices, according to a variety of conventional methods.

According to an embodiment, the image displayed in the display 830 may be a lung image of a human. If a specific matter occurs in the portion, at which the user 810 gazes, of the lung image 831, the image reading apparatus may provide diagnostic information on a suspected disease 833.

Conventionally, when determining a course of progression of a disease, since a past medical image is compared directly with the naked eye, or information recorded on a chart of the subject by the reader, it is hard to determine the disease accurately in the case that the reader is changed or moves to another clinic.

Referring to FIG. 9, the diagnostic information on the suspected disease 833 according to an embodiment may include information on temporal change of the conditions of the subject. For example, the diagnostic information on the suspected disease may include quantitative analysis information corresponding to the suspected disease. More specifically, the image reading apparatus may analyze the previous recorded information on the subject to provide quantitative analysis information over time.

The information on change of conditions according to an embodiment may include information on temporal change of size 910 of the region of interest. For example, in the event that the region of interest is a tumor, which occurs in a lung, the information on change of conditions may include a graph denoting change of tumor size according to its temporal change. In such a case, the information on change of conditions may include information which is obtainable from the currently examined slice as well as the entire image and may include information on previous medical image of the subject and image information on another subject containing the same symptoms.

The information on change of conditions according to another embodiment may include information on temporal change of a property of the region of interest 920. For example, in the event that the region of interest is a lung of the subject, the information on change of conditions may include a graph which denotes ratio change of a degree of general drift of a tissue of the lung over time and a type of the drift, when reading a diffuse interstitial lung disease (DILD).

The method according to the embodiments may be implemented as a form of program instructions capable to be executed through a variety of computer methods to be stored in a computer readable medium. The computer readable medium may contain program instructions, data files, data structures, etc., independently or in combination. The program instructions stored in the medium may be specifically designed and configured for the embodiments or available by being known to a person having ordinary skill in the computer software field. Examples of the computer readable record medium may include a magnetic medium, such as a hard disk, a floppy disk and a magnetic tape, an optical medium such as CD-ROM and DVD, a magneto-optical medium such as a floptical disk, and a hardware device specifically configured to store and perform the program instructions such as a ROM, a RAM, a flash memory, etc. Examples of the computer instructions may include machine language code as generated by a compiler as well as high-level language code which may be executed by a computer using an interpreter, etc. The above-mentioned hardware device may be configured to operate as one or more software modules for performing the operations of the embodiments and vice versa.

While certain embodiments have been described with the limited drawings, a person having ordinary skill in the art may variously modify and change them from the aforesaid. For example, a proper result may be achieved even if the described technologies are performed in an order different from the described order, and/or if the described components such as a system, structure, apparatus, circuit, etc. are connected or combined in a form different from the described, and/or if the components are substituted or replaced by another component or an equivalent. Therefore, another implementation, another embodiment and equivalents of the following claims belong to the scope of the following claims.

What is claimed is:

1. A method for increasing medical image reading efficiency, comprising:
   acquiring gaze information of a user including change of gaze and fixation time of gaze during a reading process of the medical image by the user by using a gaze tracking unit coupled with the medical image reading apparatus;
   generating, by the medical image reading apparatus, information on a region of interest (ROI) of the user based on the gaze information wherein the information on the region of interest includes the region of interest which is extracted from regions included in the medical image;
   determining, by the medical image reading apparatus, a type of service corresponding to the region of interest, using the gaze information which includes the change of gaze and the fixation time of gaze; and
   providing, by the medical image reading apparatus, the determined service, and wherein the type of service is determined to be adapted for reading efficiency of the region of interest, based on characteristics of the region of interest including the dimension of the medical image, the modality of the medical image and the morphology of the medical image, and a department in which the user is specialized,
   wherein the providing the type of service includes:
   in the event that the region of interest is a tissue or a lesion, providing, by the medical image reading apparatus, a three-dimensional model of the tissue or the lesion,
   wherein the three-dimensional model is generated based on reconstructing regions of the tissue or a lesion into a three-dimension.

2. The method of claim 1, further comprising
   analyzing, by the medical image reading apparatus, change of the gaze information of the user; and
   inferring, by the medical image reading apparatus, a suspected disease from the change of the gaze information.

3. The method of claim 2, wherein the providing the determined service further includes:
   providing, by the medical image reading apparatus, quantitative information to aid the reading or diagnosis of the suspected disease.

4. The method of claim 1, wherein the determining the type of service includes:
    searching, by the medical image reading apparatus, a brightness level and range which are required for maximizing the readability of the region of interest.

5. The method of claim 1, wherein the determining the type of service includes:
    in the event that the region of interest is a tissue or a lesion, generating, by the medical image reading apparatus, quantitative information on the tissue or the lesion.

6. The method of claim 1, wherein the determining of the type of service includes:
    in the event that a lesion or a disease is observed in the region of interest, generating, by the medical image reading apparatus, information on temporal change of the lesion or the disease.

7. A non-transitory computer readable medium having stored thereon instructions which, when executed by a computer hardware, causes the computer hardware to perform the method of claim 1 to implement the medical image reading apparatus.

8. A medical image reading apparatus, comprising:
    a gaze tracking unit tracking a gaze of a user during a medical image reading process;
    a service determining unit comprised of executable program instructions stored in a non-transitory computer readable medium for:
    generating information on a region of interest (ROI) of the user based on the gaze information which includes change of gaze and fixation time of gaze, the information on the region of interest including the region of interest which is extracted from regions included in the medical image,
    determining a type of service corresponding to the region of interest, using the gaze information which includes the change of gaze and the fixation time of gaze, and
    a service providing unit providing the determined service,
    wherein the type of service is determined to be adapted for increased reading efficiency of the region of interest, based on characteristics of the region of interest including the dimension of the medical image, the modality of the medical image, the morphology of the medical image, and a department in which the user is specialized, and
    wherein the type of service includes:
    in the event that the region of interest is a tissue or a lesion, providing a three-dimensional model of the tissue or the lesion,
    wherein the three-dimensional model is generated based on reconstructing regions of the tissue or a lesion into a three-dimension.

9. The apparatus of claim 8, wherein the service determining unit analyzes change of gaze of the user and infers a suspected disease from the change of gaze.

10. The apparatus of claim 9, wherein the service providing unit provides quantitative information to aid reading or diagnosis of the suspected disease.

11. The apparatus of claim 8, wherein the service determining unit searches a brightness level and range which are required for maximizing a readability of the region of interest.

12. The apparatus of claim 8, wherein the service determining unit generates quantitative information on a tissue or a lesion, in the event that the region of interest is the tissue or the lesion.

13. The apparatus of claim 8, wherein the service determining unit generates information on temporal change of a lesion or a disease, in the event that the lesion or the disease is observed in the region of interest.

14. The method of claim 1, wherein the providing the determined service further includes:
    providing, by the medical image reading apparatus, medical image of another subject having similar condition with the region of interest.

15. The method of claim 2, wherein the providing the determined service further includes: providing, by the medical image reading apparatus, information on how the suspected disease in the region of interest will progress in the future.

16. The apparatus of claim 8, wherein the type of service further includes:
    providing, by the medical image reading apparatus, medical image of another subject having similar condition with the region of interest.

17. The apparatus of claim 9, wherein the type of service further includes: providing, by the medical image reading apparatus, information on how the suspected disease in the region of interest will progress in the future.

* * * * *